(12) United States Patent
Yamashita et al.

(10) Patent No.: US 6,919,372 B1
(45) Date of Patent: Jul. 19, 2005

(54) SUSTAINED RELEASE PHARMACEUTICAL COMPOSITIONS

(75) Inventors: Noboru Yamashita, Shizuoka Ken (JP); Akira Takagi, Shizuoka Ken (JP); Masataka Katsuma, Shizuoka Ken (JP); Katsumi Saito, Shizuoka Ken (JP); Yuuki Takaishi, Shizuoka Ken (JP); Tatsuo Yasuda, Shizuoka Ken (JP); Yutaka Takahashi, Shizuoka Ken (JP); Mitsuo Mitomi, Shizuoka Ken (JP); Michio Hara, Kanagawa-ken (JP)

(73) Assignee: Yamanouchi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/582,404

(22) PCT Filed: Dec. 25, 1998

(86) PCT No.: PCT/JP98/05915

§ 371 (c)(1),
(2), (4) Date: Jun. 23, 2000

(87) PCT Pub. No.: WO99/33490

PCT Pub. Date: Jul. 8, 1999

(30) Foreign Application Priority Data

Dec. 26, 1997 (JP) ............................................. 97360265

(51) Int. Cl.$^7$ ........................ A01N 43/08; A61K 31/34
(52) U.S. Cl. ..................................................... 514/468
(58) Field of Search ......................................... 514/468

(56) References Cited

FOREIGN PATENT DOCUMENTS

| JP | 02262519 | * 10/1990 |
| JP | 2-300109 | 12/1990 |
| JP | 4-41432 | 2/1992 |
| JP | 04356422 | * 12/1992 |
| JP | 5-238959 | 9/1993 |
| WO | 9857972 | * 12/1998 |

OTHER PUBLICATIONS

Hirano et al, Pharmacokinetics and biotransformation of beraprost sodium, 1989, vol. 4, No. 6, pp. 779–792.*

* cited by examiner

Primary Examiner—Alton Pryor
(74) Attorney, Agent, or Firm—Townsend and Townsend and Crew LLP (57) ABSTRACT

The present invention relates to sustained-release pharmaceutical compositions for ionic pharmaceutically active substances containing ionic compounds having opposite charges to those of ionic prostanoic acid derivatives and increasing hydrophobicity of the active substances. More specifically, the invention relates to sustained-release pharmaceutical compositions comprising the ionic prostanoic acid derivatives and the ionic compounds having opposite charges to those of the prostanoic acid derivatives and increasing hydrophobicity of these derivatives that contain hydrophobic groups in the molecule thereof.

The pharmaceutical composition of the invention can exhibit excellent sustained release effect of the ionic prostanoic acid derivatives, irrespective of water solubility possessed by the ionic prostanoic acid derivatives.

10 Claims, 2 Drawing Sheets

SUSTAINED RELEASE PHARMACEUTICAL COMPOSITIONS

FIELD OF THE INVENTION

The present invention relates to a sustained-release pharmaceutical composition for an ionic prostanoic acid derivative. More particularly, the invention relates to a sustained-release pharmaceutical composition comprising an ionic prostanoic acid derivative and an ionic compound which has an opposite charge to that of the ionic prostanoic acid derivative and enhances the hydrophobic property of the ionic prostanoic acid derivative.

RELATED ART

Oral administration has been widely applied to delivery of pharmaceutically active substances. While there is a need for fast-acting drugs, both fast and continuously acting drugs are simultaneously necessary sometimes. In this case, parenteral administration is generally used in combination with oral administration. For parenteral preparations, there are known intravenous, subcutaneous or intramuscular injection; implants and transmucosal preparations through oral cavity, nasal cavity, lung, vagina, rectum, skin, etc. Of these routes, injection is a general choice for administration.

However, sustained release of some medicaments may cause difficulty in parenteral preparations, depending upon the property of a pharmaceutically active substance. For example, such difficulty is noted with pharmaceutically active substances having a short half life in blood, a high water solubility or a low molecular weight. When it is desired to maintain the pharmacological effects of those medicaments over a long period of time, it is the actual practice to administer such a medicament by instillation through the vein or frequently inject the medicament subcutaneously or intramuscularly. A burden of such a treatment is not negligible to patients either physically or mentally. To solve the problem, it has been investigated to create a pharmaceutically active substance having a prolonged half life in blood or to produce a hybrid between a pharmaceutically active substance and a high molecular weight substance such as polyethylene glycol by irreversible bonding of the two substances, thereby to extend the half life of the pharmaceutically active substance itself in blood. Various other techniques for controlling the solubility or dissolution of a pharmaceutically active substance out of a carrier have been studied, which involve insolubilizing or sparingly solubilizing a pharmaceutically active substance in water to delay its dissolution, or microencapsulation of a pharmaceutically active substance using a biodegradable high molecular weight material.

For example, Japanese Patent Application Laid-Open No. 1-163199 discloses that an organic acid with a high molecular weight of about 5,000 or more, e.g., sodium alginate, is added to a cytokine like interleukin 2 so as to reach the isotonic osmotic pressure or more and the mixture is then shaken to form the water-insoluble matter, whereby the insoluble mater is used in a sustained-release composition for injection.

Japanese Patent Application Laid-Open No. 9-208485 discloses a sustained-release preparation comprising a sparingly water-soluble composition formed from a peptide-proteinaceous medicament and EDTA.

Japanese Patent Application Laid-Open Nos. 8-3055 and 8-217691 disclose sustained-release preparations comprising microcapsules obtained by mixing a water-soluble pharmaceutically active substance and a water-soluble polyvalent metal salt, and dispersing the resulting water-insoluble mixture of in a biodegradable high molecular weight material such as polylactic acid-glycolic acid copolymer.

On the other hand, Japanese Patent Application Laid-Open No. 62-129226 discloses that hyaluronic acid or its sodium salt, or Hylan enables a medicament dissolved or dispersed in the solution to achieve continuous release from the solution mainly based on the viscosity of the solution. This publication also discloses that in a cationic group-containing medicament, exchange of ions could occur between this carboxyl group-containing macromolecule of hyaluronic acid and the medicament, where the exchange causes slower diffusion of the medicament out of the system. As a technique utilizing the viscosity of hyaluronic acid, Japanese Patent Application Laid-Open No. 1-287041 discloses a sustained-release preparation suitable for subcutaneous or intramuscular administration, comprising a pharmaceutically active substance and hyaluronic acid or a salt thereof, Japanese Patent Application Laid-Open No. 2-213 also discloses a sustained-release preparation comprising a physiologically active peptide and hyaluronic acid or a salt thereof.

However, such a sustained-release preparation utilizing the viscosity of hyaluronic acid provides a fast diffusion of a pharmaceutically active substance from the viscous product, in which the active substance is incorporated. Even taking into account the ionic interaction ability between hyaluronic acid and a cationic medicament coupled to the viscosity of hyaluronic acid, it is suspected that retardation in dissolution is not enough. Yet, any sustained-release parenteral preparation that is satisfactory from a clinical standpoint has been unknown for not only cationic but also ionic pharmaceutically active substances. Particularly in the case of a highly water-soluble ionic pharmaceutically active substance, sustained release could not be attained to a satisfactory extent by the prior art technique of retarding the diffusion using the viscosity of a high molecular weight substance, especially because of its high water solubility.

Japanese Patent Application Laid-Open No. 53-18723 discloses a composition for rectal administration obtained by intimately mixing insulin with a quaternary ammonium salt cationic surfactant. Japanese Patent Application Laid-Open No. 59-89619 discloses a liquid pharmaceutical composition for nasal administration, comprising calcitonin and benzalkonium chloride in a liquid diluent or carrier suitable for application to nasal mucous membrane. However, the techniques described in these gazette publications all aim at improving absorption of a medicament by rectal administration or nasal administration but none of the publications mentions or even suggests sustained release of a medicament involving the imparted hydrophobic property of an ionic complex.

DISCLOSURE OF THE INVENTION

An object of the present invention is to provide a sustained-release preparation of an ionic prostanoic acid derivative, irrespective of water solubility of the ionic prostanoic acid derivative, to such an extent that is satisfactory for clinical use.

The present inventors attempted to provide a sustained-release preparation for an ionic prostanoic acid derivative, for which sustained release is required through parenteral route, first by adding an equimolar amount of a cationic compound to the anionic prostanoic acid derivative and forming a sparingly water-soluble ionic complex through ionic interaction between the anionic derivative and the cationic compound, with an expectation to achieve a sustained release of the anionic prostanoic acid derivative. However, subcutaneous administration of the ionic complex formed to rats revealed that no satisfactory sustained-release was obtained. It was thus found that the retarded dissolution of ionic prostanoic acid derivatives is insufficient for the purpose of sustained release of ionic pharmaceutically active substances by parenteral route.

In order to further increase the hydrophobicity of the pharmaceutically active substance accompanied by the formation of the ionic complex, the present inventors have brought attention to an octanol/water partition coefficient as an index for the hydrophobicity. As a result, it has been found that depending upon kind of the cationic compound, there is a difference in the octanol/water partition coefficient of the anionic prostanoic acid derivative associated with the ionic complex formation and that a better sustained release effect is obtained with a larger partition coefficient. It has also been found that the sustained release effect can be more enhanced by increasing the addition amount of the cationic compound and increasing the partition coefficient for the anionic pharmaceutically active substance. Furthermore, it has been discovered that these ionic complexes unexpectedly exhibit an excellent sustained release effect, even when a dissolved state of the pharmaceutically active substance in water is maintained, that is, the state of its aqueous solution is maintained if the pharmaceutically active substance is water-soluble.

The present inventors have found that a sustained release of the ionic pharmaceutically active substance attained by increasing the hydrophobicity of an ionic pharmaceutically active substance was hitherto unknown and that this sustained release technique can be advantageously applied not only to parenteral preparations but to oral preparations. Based on the finding, the present invention has been found.

(1) That is, the present invention relates to a sustained-release pharmaceutical composition comprising an ionic prostanoic acid derivative and an ionic compound having an opposite charge to that of the ionic prostanoic acid derivative and increasing hydrophobicity of the derivative.

(2) The present invention also relates to a sustained-release pharmaceutical composition according to (1), wherein the ionic compound having an opposite charge to that of the ionic prostanoic acid derivative and increasing the hydrophobic property of the derivative contains a hydrophobic group in the molecule thereof.

(3) The present invention also relates to a sustained-release pharmaceutical composition according to (1) or (2), wherein the ionic compound increases an oil/water partition coefficient of the ionic prostanoic acid derivative.

(4) The present invention further relates to a sustained-release pharmaceutical composition according to any one of (1) to (3), wherein the ionic compound is incorporated at least in an equimolar amount based on the ionic prostanoic acid derivative in terms of a charge ratio.

The sustained-release pharmaceutical composition of the present invention is characterized in that by adding a particular counter ion to the ionic prostanoic acid derivative to increase the oil/water partition coefficient of the ionic pharmaceutically active substance, a hydrophobic property is imparted to give the sustained-release pharmaceutical composition of the invention suitable for, e.g., injection. The sustained release according to the present invention is effected by means of a novel method quite different from conventional techniques adopted to control the release of ionic pharmaceutically active substances, to insolubilize a pharmaceutically active substance itself, to retard the dissolution of the active substance by microencapsulation, etc. Moreover, the present invention is characterized in that the sustained release can be achieved by the composition of the invention to a fully satisfactory extent that was obtained only insufficiently by these known means.

The sustained-release pharmaceutical composition of the present invention will be described below in more detail.

In general, ionic prostanoic acid derivatives refer to ionic prostaglandins $A_2$, $B_2$, $C_2$, $D_2$, $E_2$, $F_{2a}$, $G_2$, $H_2$, $I_2$ and $J_2$ and these derivatives can be used in the present invention without any particular restriction, so long as they are provided conventionally for a pharmacological treatment and their sustained release is desired for oral or parenteral administration. Preferred examples of the ionic prostanoic acid derivative are prostaglandin $I_2$ derivatives. More preferably, the ionic prostanoic acid derivative is represented by the following general formula (I):

wherein $R^1$ represents $COOR^2$ (wherein $R^2$ represents:
1) hydrogen or a pharmacologically acceptable cation,
2) —Z—$Ar^1$, wherein Z is a valence bond or a straight or branched alkylene shown by $C_tH_{2t}$ wherein t is an integer of 1 to 6, and $Ar^1$ is 2-pyridyl, 3-pyridyl or 4-pyridyl;
3) —$C_tH_{2t}$ $COOR^3$, wherein $C_tH_{2t}$ has the same significance as defined above, and $R^3$ is hydrogen or a pharmacologically acceptable cation;

or,

4) —$C_tH_{2t}N(R^4)_2$, wherein $C_tH_{2t}$ has the same significance as defined above, and $R^4$ is hydrogen, a straight alkyl having 1 to 12 carbon atoms or a branched alkyl having 3 to 14 carbon atoms);

A represents:
1) —$(CH_2)_m$—, wherein m is an integer of 1 to 3;
2) —CH=CH—$CH_2$—;
3) —$CH_2$—CH=CH—;
4) —$CH_2$—O—$CH_2$—;
5) —CH=CH—;
6) —O—$CH_2$—; or,
7) —C≡C—;

Y represents hydrogen, an alkyl having 1 to 4 carbon atoms, chlorine, bromine, fluorine, formyl, methoxy or nitro;

B represents —X—C($R^5$)($R^6$)$OR^7$ (wherein $R^5$ represents hydrogen or an alkyl having 1 to 4 carbon atoms; $R^7$ represents hydrogen, an acyl having 1 to 14 carbon atoms, an aroyl having 6 to 15 carbon atoms, tetrahydropyranyl, tetrahydrofuranyl, 1-ethoxyethyl or t-butyl; X represents:
1) —$CH_2$—$CH_2$—;
2) —CH=CH—; or
3) —C≡C—;

$R^6$ represents:
1) a straight alkyl having 1 to 12 carbon atoms or a branched alkyl having 3 to 14 carbon atoms;
2) —Z—$Ar^2$, wherein Z has the same significance as defined above and $Ar^2$ is phenyl, α-naphthyl, β-naphthyl or a phenyl substituted with at least one of chlorine, bromine, fluorine, iodine, trifluoromethyl, an alkyl having 1 to 4 carbon atoms, nitro, cyano, methoxy, phenyl or phenoxy;
3) —$C_tH_{2t}OR^8$, wherein $C_tH_{2t}$ has the same significance as defined above, and $R^8$ is a straight alkyl having 1 to 6 carbon atoms, a branched alkyl having 3 to 6 carbon atoms, phenyl, a phenyl substituted with at least one of chlorine, bromine, fluorine, iodine, trifluoromethyl, an alkyl having 1 to 4 carbon atoms, nitro, cyano, methoxy, phenyl or phenoxy, cyclopentyl, cyclohexyl, or a cyclopentyl or cyclohexyl substituted with 1 to 4 straight alkyl group(s) having 1 to 4 carbon atoms;
4) —Z—$R^9$, wherein Z has the same significance as defined above, and $R^9$ is hydrogen, a cycloalkyl having 3 to 12 carbon atoms or a substituted cycloalkyl having 3 to 12 carbon atom which is substituted with 1 to 3 alkyl groups having 1 to 5 carbon atoms;
5) —$C_tH_{2t}$—CH=C($R^{10}$)$R^{11}$ wherein $C_tH_{2t}$ has the same significance as defined above, and $R^{10}$ and $R^{11}$ represent hydrogen, methyl, ethyl, propyl or butyl; or
6) —$C_uH_{2u}$—C≡C—$R^{12}$, wherein u is an integer of 1 to 7, $C_uH_{2u}$ is a straight or branched alkylene and $R^{12}$ is a straight alkyl having 1 to 6 carbon atoms);

E represents hydrogen or —$OR^{13}$, wherein $R^{13}$ is hydrogen, an acyl having 1 to 12 carbon atoms, an aroyl having 7 to 18 carbon atoms, a straight alkyl having 1 to 12 carbon atoms or a branched alkyl having 3 to 14 carbon atoms;
or salts thereof.

In some of the compounds represented by general formula (I) described above, optical isomers may be present based on an asymmetric carbon in the molecule. The present invention covers all of d-, l- and dl-isomers.

As more preferred ionic prostaglandin $I_2$ derivatives, the compounds which are excellent in stability are chosen. Examples of such prostaglandin $I_2$ derivatives are Iloprost, Clinprost, Ataprost, Ciprostene, Naxaprostene, Taprostene, Cicaprost, Pimilprost, CH-169, SM-10902, CS570, etc. and salts or esters thereof. Preferred examples also include the compounds which can be produced by the process described in Japanese Patent Application Laid-Open No. 58-124778, or salts thereof, more preferably, (±)-(1R*,2R*,3aS*,8bS*)-2,3,3a,8b-tetrahydro-2-hydroxy-1-[(e)-(3S*)-3-hydroxy-4-methyl-1-octen-6-ynyl]-1H-cyclopenta[b]benzofuran-5-butanoic acid (generic name "beraprost") or salts thereof (the sodium salt of beraprost is commercially available as an anti-platelet agent or a blood flow improving agent under the generic name "beraprost sodium", which is sometimes abbreviated as "BPS").

The amount of the ionic prostanoic acid derivative used in the present invention is not particularly limited as far as it is within such an amount that exhibits a pharmacologically therapeutic effect. In the case of, e.g., BPS, the amount is in the range of 0.1 to 1,000 μg. According to the present invention, even if a substance is sparingly soluble in water, the ionic prostanoic acid derivative can enjoy the benefits of sustained release by imparting hydrophobicity, as in readily water-soluble substances.

The ionic compound having an opposite charge to that of the ionic prostanoic acid derivative and increasing its hydrophobicity used in the present invention is not particularly restricted but preferably a substance containing a highly hydrophobic group(s). The presence of highly hydrophobic group(s) in the molecule of the ionic compound can increase the hydrophobic property of the ionic prostanoic acid derivative. The degree of hydrophobicity can be determined by calculating as an index the oil/water partition coefficient of the pharmaceutically active substance (that is, a ratio of, e.g., the concentration of the pharmaceutically active substance in an oil phase such as octanol to the concentration of the pharmaceutically active substance in water). Preferably, when the ionic compound is added to the ionic prostanoic acid derivative in such an amount that the compound has a charge equivalent to that of the prostanoic acid derivative, the oil/water partition coefficient increases as compared to no addition of the compound. More preferably, when the compound having a counter ion is added to the ionic prostanoic acid derivative in an excess amount to give more charges by, e.g., 20 times than equivalent one, the partition coefficient increases much more than the addition in an equivalent charge. The term "ionic" in the ionic compound of the present invention is used to mean that the compound contains one or more charged groups in the molecule thereof. The charged group functions as a hydrophilic group in the molecule. The ionic compound may additionally contain other hydrophilic groups not associated with charge. Preferably, the ionic state contains one charged group in the molecule thereof. The cationic compound to be incorporated preferably contains an ammonium, pyridinium, phosphonium or sulfonium group in the molecule thereof, or may be in the form of their salts. More preferably, the cationic compound contains the functional group above mentioned and the functional group carries a hydrophobic group having at least 6 carbon atoms. Examples of such cationic compounds are trialkylbenzyl ammonium salts such as benzyltriethylammonium chloride, benzyltributylammonium chloride, etc.; alkyldimethylbenzylammonium salts such as octyldimethylbenzylammonium chloride, lauryldimethylbenzylammonium chloride, myristyldimethylbenzylammonium chloride, stearyldimethylbenzylammonium chloride, benzalkonium chloride which is the mixture of lauryldimethylbenzylammonium chloride and myristyldimethylbenzylammonium chloride; benzethonium chloride or derivatives thereof; alkyltrimethyl salts such as lauryltrimethylammonium chloride, cetyltrimethylammonium chloride, lauryltrimethylammonium chloride, behenyltrimethylammonium chloride, etc.; alkyl pyridinium salts such as laurylpyridinium chloride, cetylpyridinium chloride, etc.; alkylamine salts such as oleylamine acetate, stearylamine acetate, etc.; alkylphosphonium salts such as tetrabutylphosphonium chloride, tricetyl(4-vinylbenzyl) phosphonium chloride, etc. or derivatives thereof. Examples of the cationic compounds include surface-active medicaments such as chlorpromazine hydrochloride, phenothiazine, perphenazine, perphenazine maleate, levomepromazine, lidocaine hydrochloride, meprylcaine hydrochloride, acetylcholine chloride, methylbenactyzium bromide, distigmine bromide, torazoline hydrochloride, imipramine hydrochloride, desipramine hydrochloride, amitriptyline hydrochloride, procaine hydrochloride, lidocaine hydrochloride, dibucaine hydrochloride, meprylcaine, diphenhydramine hydrochloride, chlorpheniramine maleate, iproheptine, etc. These cationic compounds may be in the form of pharmaceutically acceptable salts or free bases. Preferably, the salts are alkyldimethylbenzylammonium salts, alkyldimethylbenzylammonium salts, alkylpyridinium salts, alkylamine slats and alkylphosphonium salts, more preferably, alkyldimethylbenzylammonium salts, most preferably benzalkonium chlorides. These compounds may be used in combination of two or more.

In case that the pharmaceutically active substance is cationic, the anionic compound added as the ionic compound in the present invention contains preferably a carboxyl, sulfate, sulfonate or phosphate group in the molecule thereof. More preferably, the anionic compound contains the functional group(s) described above which carries a hydrophobic group of at least 6 carbon atoms. Examples of such anionic compounds include higher fatty acids such as caproic acid, caprylic acid, capric acid, lauric acid, myristic acid, palmitic acid, stearic acid, oleic acid, etc. or physiologically acceptable salts thereof (e.g., sodium or potassium); alkyl sulfates such as sodium lauryl sulfate, sodium myristyl sulfate, etc.; alkyl ether sulfates such as POE (2) lauryl ether sodium sulfate, etc.; alkylallyl sulfonates such as sodium lauryl sulfoacetate, etc.; alkyl sulfonates such as sodium dodecylbenzenesulfonate, etc.; sulfosuccinates; N-acylaminoacid salts such as sodium lauroylsarcosine, etc.; alkyl phosphates such as sodium laurylphosphate, etc.; alkyl ether phosphates or free acids thereof; bile acids or salts thereof such as sodium deoxycholate, etc.; and dialkylphosphatidinic acid salts such as sodium dipalmitoylphosphatidinate, etc. or free acids thereof. Preferably, the anionic compounds are sodium oleate and/or sodium laurylsulfate. These compounds may be used in combination of two or more.

The amount of the ionic compound to be added is not particularly limited so long as the compound is added in such an amount that can generally neutralize the charge of the ionic prostanoic acid derivative and increase the hydrophobic property of the prostanoic acid derivative. The ionic compound is added preferably in the amount of 0.0001% to 50%, more preferably 0.001 to 10%, most preferably 0.01 to 5%, all inclusive, in terms of weight % by weight. The amount of the ionic compound to be added can be chosen to be the amount showing a desired sustained release pattern within the physiologically acceptable upper limit. The amount of the ionic compound added can be determined generally in terms of a molar ratio (charge ratio) based on the ionic prostanoic acid derivative and is preferably between 1 and 1,000, inclusive.

With respect to the pH of the sustained-release pharmaceutical composition of the present invention, its pH range is not particularly limited as far as pH is generally within a physiologically acceptable range but preferably it is in the range of 3 to 8. The pH can be suitably determined in view of stability of the ionic prostanoic acid derivative used in the invention.

The sustained-release pharmaceutical composition of the present invention can be prepared into a variety of pharmaceutical preparations in the form of, e.g., an aqueous solution, an oily preparation, a fatty emulsion, an emulsion, a gel, etc., and these preparations can be administered as intramuscular or subcutaneous injection or as injection to the organ, or as an implant or as a transmucosal preparation through nasal cavity, rectum, uterus, vagina, lung, etc. The composition of the present invention can also be administered in the form of oral preparations (e.g., solid preparations such as tablets, capsules, granules or powders; liquid preparations such as syrup, emulsions or suspensions). Inter alia, injection is a preferred form of the preparations. Where the composition is prepared into an injection, the composition may contain, if necessary and desired, a known preservative, stabilizer, dispersing agent, pH controller or isotonic agent. Examples of the preservative are glycerin, propylene glycol, phenol, benzyl alcohol, etc. Examples of the stabilizer are dextran, gelatin, tocopherol acetate, alpha-thioglycerin, etc. Examples of the dispersing agent include polyoxyethylene (20) sorbitan monooleate (Tween 80), sorbitan sesquioleate (Span 30), polyoxyethylene (160) polyoxypropylene (30) glycol (Pluronic F68), polyoxyethylene hydrogenated castor oil 60, etc. Examples of the pH controller include hydrochloric acid, sodium hydroxide, etc. Examples of the isotonic agent are glucose, D-sorbitol, D-mannitol, etc.

The sustained-release pharmaceutical composition of the present invention can be administered as an aqueous solution in its original composition since the composition itself exhibits the sustained release effect. In order to further enhance the sustained release effect, however, the composition may be formulated with additional components such as vegetable oil, e.g., soybean oil, sesame oil, camellia oil, castor oil, peanut oil, rape seed oil, etc.; middle fatty acid triglycerides; fatty acid esters such as ethyl oleate; polysiloxane derivatives, etc.; alternatively, water-soluble high molecular weight compounds such as hyaluronic acid or salts thereof (weight average molecular weight: ca. 80,000 to 2,000,000), carboxymethylcellulose sodium (weight average molecular weight: ca. 20,000 to 400,000), hydroxypropylcellulose (viscosity in 2% aqueous solution: 3 to 4,000 cps), atherocollagen (weight average molecular weight: ca. 300,000), polyethylene glycol (weight average molecular weight: ca. 400 to 20,000), polyethylene oxide (weight average molecular weight: ca. 100,000 to 9,000,000), hydroxypropylmethylcellulose (viscosity in 1% aqueous solution: 4 to 100,000 cSt), methylcellulose (viscosity in 2% aqueous solution: 15 to 8,000 cSt), polyvinyl alcohol (viscosity: 2 to 100 cSt), polyvinylpyrrolidone (weight average molecular weight: 25,000 to 1,200,000), etc.

In the sustained-release pharmaceutical composition of the invention, it is preferred that the ionic prostanoic acid derivative be maintained in its dissolution state but may be in the form of a suspension, since there is no particular limitation to the appearance.

Disorders to which the sustained-release pharmaceutical composition of the invention are applicable are not particularly limited. Because of diverse therapeutic effects possessed by prostaglandin I derivatives, the sustained-release pharmaceutical composition of the invention can be used for improving peripheral circulation, as an antithrombotic agent, as an antihypertensive agent, for the treatment of heart failure, various complications accompanied by diabetes, peptic ulcer, skin ulcer, hyperlipemia and asthma, etc.

A dose of the sustained-release pharmaceutical composition according to the present invention may be appropriately chosen, depending upon the amount of the composition or the pharmaceutically active substance contained in the composition, kind of diseases, age and body weight of the patient, frequency of administration, etc. In the case of using, e.g., BPS, the dose is in the range of 0.1 μg to 10 g, preferably 10 μg to 1 g.

BEST MODE FOR CARRYING OUT THE INVENTION

The present invention will be described below in more detail, with reference to Tests, Examples and Comparative Examples.

Test 1

Figure 1:
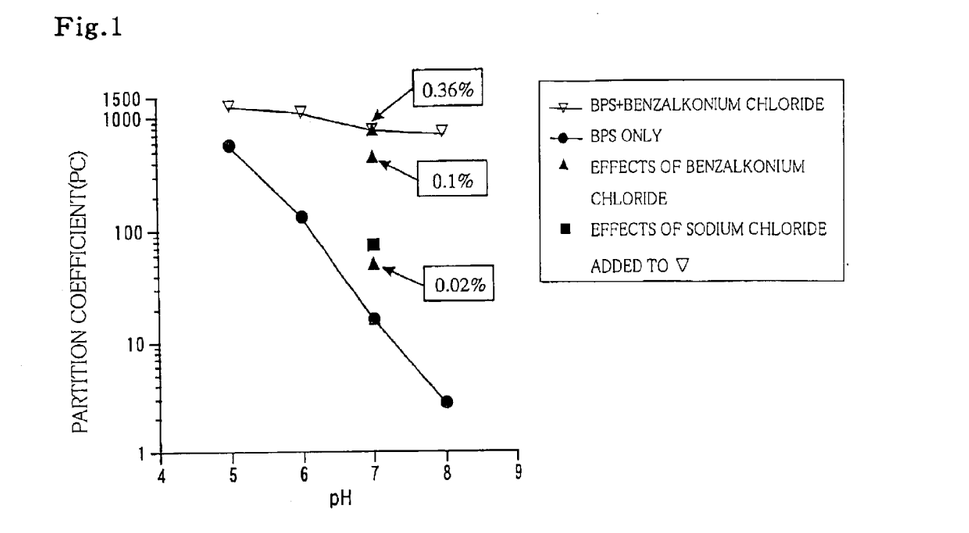
FIG. 1 shows relationship between the ratio of the cationic compound added and pH in octanol/phosphate buffer partition coefficient (PC) of BPS.

Effect of the Ratio of Benzalkonium Chloride Added and pH in the Octanol/Phosphate Buffer Partition Coefficient (PC) of BPS Method:

BPS was dissolved in phosphate buffer solution having pH of 5 to 8 in a concentration of 240 μg/ml. Various cations were added to the mixtures to give equivalent charge to that of BPS or 5 times or 20 times more than that of BPS. The same volume of octanol as that of the aqueous phase was added to the mixture followed by shaking at 37° C. for an hour. After centrifugation, the concentration of the pharmaceutically active substance in the aqueous phase was measured to calculate the partition coefficient.

partition coefficient=concentration of the pharmaceutically active substance in the octanol phase/concentration of the pharmaceutically active substance in the aqueous phase Results and Discussion:

FIG. 1 shows the relationship between the ratio of the cationic compound added and pH on octanol/phosphate buffer partition coefficient(PC) of BPS As a result, PC increased at pH of 7 as the amount of benzalkonium chloride added increased. This is considered to be because BPS with its hydrophobic degree being increased by the formation of ion complex is distributed in the octanol phase so that the equilibrium in the ion complex formation occured in the aqueous phase shifted toward the complex formation as the concentration of benzalkonium chloride became high. With respect to the pH, the partition coefficient of BPS, which is an acidic substance, decreased as the pH increased but the decrease in partition coefficient was suppressed by the addition of benzalkonium chloride. That is, the effect of benzalkonium chloride on the partition coefficient of BPS was greater in the high pH. When sodium chloride was added to make the solution isotonic, in which 20 times of equivalent molar ratio of benzalkonium chloride was included, the partition coefficient of BPS decreased. This is believed to be because the formation of ionic complex would be inhibited by the addition of sodium chloride. It was thus supported that the formation of ionic complex participated in the effect of enhancing the partition coefficient of BPS achieved by the addition of benzalkonium chloride.

Test 2

Evaluation of Cationic Compound by Test in Terms of Partition Coefficient

A variety of cations were examined with their effect if these cations would affect the partition coefficient of BPS in octanol/phosphate buffer solution (pH 7).

Method:

The pharmaceutically active substance was dissolved in an aqueous phase in a concentration of 240 μg/ml. Various cations were added to the solution to give equal charge to that of the pharmaceutically active substance or charges 20 times more than that of the substance. Then the same procedure as in Test 1 was applied to calculate the partition coefficient.

Results and Discussion:

With regard to the effect of various cations on the partition coefficient of the ionic prostanoic acid derivative, representative results are shown in Table 1. An increase in the partition coefficient of the ionic prostanoic acid derivative was noted with alkylbenzylammonium salts such as triethylbenzylammonium chloride, etc., alkyltrimethylammonium salts such as lauryltrimetnylammonium chloride, etc.; phosphonium salts, lidocaine hydrochloride and meprylcaine hydrochloride. However, the partition coefficient of BPS showed no change with sorbitan sesquioleate (Span 30), which is a nonionic compound, and sodium lauryl sulfate, which is an anionic compound, for comparison, as compared to the partition coefficient when any ionic compound was not added (data not shown in Table 1); the results indicate that no effect was observed with the comparative compounds. Turning to the inorganic salts (magnesium chloride) or the compound having a small level of hydrophobicity (arginine hydrochloride), these compounds could form complexes but failed to enhance the hydrophobic property of BPS. Thus, no increase in the partition coefficient was noted. Furthermore, cationic hydroxyethylcellulose (Kachi-sero H-60, produced by Kao Corp.) and protamine sulfate did not affect the partition coefficient; it is likely that these compounds contain hydrophilic groups represented by cationic groups so that even overall the highly hydrophilic nature of molecule is presented, the hydrophobic property of the pharmaceutically active substance would not be given enough if complexes are formed.

TABLE 1

PC of BPS

| Cation added | Equimolar amount | Excess × 20 |
|---|---|---|
| Triethylbenzylammonium chloride | — | — |
| Tributylbenzylammonium chloride | 24.5 | 140 |
| Octyldimethylbenzylammonium chloride | 60.9 | 568 |
| Lauryldimethylbenzylammonium chloride | 71.2 | 1220 |
| Myristyldimethylbenzylammonium chloride | 64.5 | 1210 |
| Stearyldimethylbenzylammonium chloride | 62.3 | 1350 |
| Benzethonium chloride | 70.8 | 1180 |
| Lauryltrimethylammonium chloride | 83.5 | 985 |
| Cetyltrimethylammonium chloride | 91.6 | 935 |
| Stearyltrimethylammonium chloride | 83.4 | 995 |
| Behenyltrimethylammonium chloride | 59.5 | — |
| Laurylpyridinium chloride | 75.0 | 1200 |
| Cetylpyridinium chloride | 77.8 | 1070 |
| Oleylamine acetate | 30.4 | 473 |
| Stearylamine acetate | 32.6 | 158 |
| Lidocaine hydrochloride | 17.1 | 37.5 |
| Meprylcaine hydrochloride | 17.7 | 53.3 |
| Tetrabutylphosphonium chloride | — | |
| Tricetyl (4-vinylbenzyl)phosphonium chloride | — | |
| None | 16.2 | |

That is, the results reveal that the compounds having opposite charges such as quaternary ammonium or phosphonium groups and highly hydrophobic substutients (e.g., hydrophobic groups of 6 or more carbon atoms) exhibit the effect of increasing the hydrophobic property of the ionic prostanoic acid derivative.

EXAMPLE 1

Gel Preparation:

After 0.024 part by weight (hereinafter merely referred to as "part") of BPS and 0.29 part of capryldimethylbenzylammonium chloride (which molar amount was adjusted to correspond to 0.36 part of benzalkonium chloride) were dissolved in 89.686 parts of water, 10 parts of hydroxypropylcellulose (trademark: HPC-M) was added to the solution. The mixture was stirred and fully swollen to give a gel preparation.

EXAMPLES 2 THROUGH 9

Gel Preparation:

Gel preparations having the same parts as in Example 1 were prepared in a manner similar to Example 1 except that capryldimethylbenzylammonium chloride of Example 1 was replaced by other cationic compounds shown in Table 2.

Table 2

TABLE 2

| Example | Cationic compound |
|---|---|
| 2 | Lauryldimethylbenzylammonium chloride |
| 3 | Myristyldimethylbenzylammonium chloride |
| 4 | Stearyldimethylbenzylammonium chloride |
| 5 | Lauryltrimethylammonium chloride |
| 6 | Cetyltrimethylammonium chloride |
| 7 | Stearyltrimethylammonium chloride |
| 8 | Behenyltrimethylammonium chloride |
| 9 | Benzethonium chloride |

COMPARATIVE EXAMPLES 1 THROUGH 3

After 0.024 part of BPS was dissolved in water, 10 parts of HPC-M was added to the solution. The mixture was then fully swollen to give a gel preparation. Furthermore, arginine hydrochloride and magnesium sulfate were added to the above preparation, respectively to give gel preparations. These preparations were used as comparative samples (Table 3).

TABLE 3

| | Comparative Reference | | |
|---|---|---|---|
| | 1 | 2 | 3 |
| BPS | 0.024 | 0.024 | 0.024 |
| Arginine hydrochloride | — | 0.1 | — |
| Magnesium sulfate 7H$_2$O | — | — | 0.1 |
| HPC-M | 10 | 10 | 10 |
| Water | 89.976 | 89.876 | 89.876 |

Test 3

In vitro Release Test of Gel Preparation Using Various Cations:

Each of the gel preparations obtained in Examples 1 to 9 and Comparative Examples 1 to 3 was evaluated, respectively, with regard to the release of the active substance in 10 ml of a phosphate buffer solution (pH 7.4) at 37° C.

According to the results, a delayed release was confirmed with the quaternary ammonium salt that was shown to enhance the hydrophobic property in the partition coefficient test (Test 2). On the other hand, no delayed release was noted with magnesium sulfate and arginine hydrochloride in the test, which are divalent inorganic metal salts similar to magnesium chloride demonstrated to hardly enhance the partition coefficient. These results thus suggest that there is a correlation between the effect of enhancing the partition coefficient and the sustained release effect.

EXAMPLE 10

Gel Preparation:

After 0.024 part of BPS and 0.02 part of benzalkonium chloride were dissolved in 89.956 parts of water, 10 parts of HPC-M was added to the solution. The mixture was stirred and fully swollen to give a gel preparation.

EXAMPLES 11 THROUGH 17

Gel Preparation:

Gel preparations having the amounts of BPS, benzalkonium chloride, HPC-M and water shown in Table 4 were prepared in a manner similar to Example 10

COMPARATIVE EXAMPLE 4

A gel preparation for comparison was prepared in a manner similar to Example 17 except that no benzalkonium chloride was added.

TABLE 4

| | Example | | | | | | |
|---|---|---|---|---|---|---|---|
| | 11 | 12 | 13 | 14 | 15 | 16 | 17 |
| BPS | 0.024 | 0.024 | 0.024 | 0.002 | 0.002 | 0.002 | 0.002 |
| Benzalkonium chloride | 0.1 | 0.2 | 0.36 | 0.002 | 0.1 | 0.2 | 0.36 |
| HPC-M | 10 | 10 | 10 | 5 | 5 | 5 | 5 |
| Water | 89.876 | 89.776 | 89.616 | 94.996 | 94.898 | 94.798 | 94.638 |

Test 4

Effect of the Amount of Counter Ions Added on Release in Gel Preparation:

Release test was carried out in 10 ml of a phosphate buffer solution (pH 7.4) at 37° C., using the preparations obtained in Reference Examples 11 through 13 and Comparative Example 1.

Figure 2:
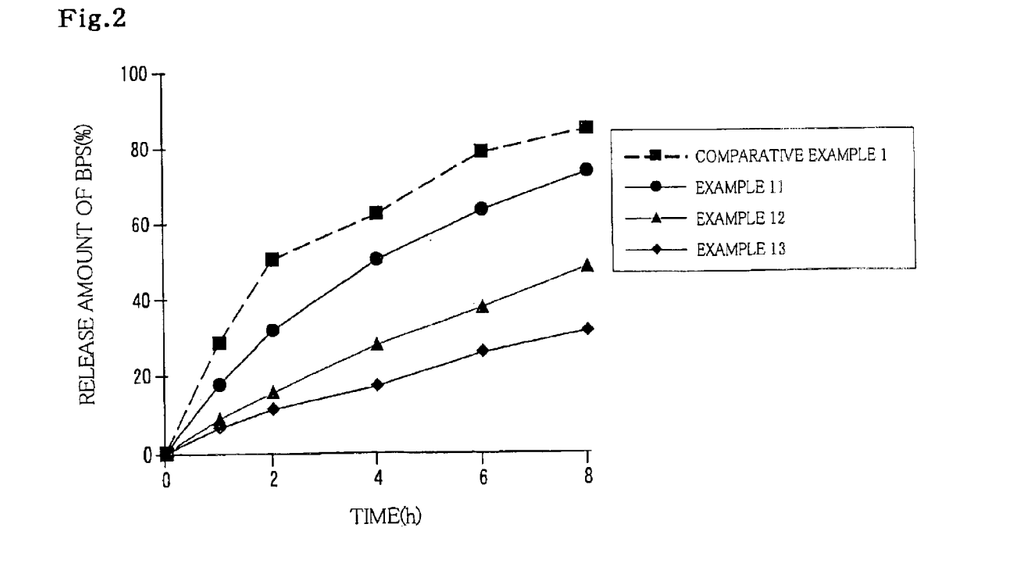
FIG. 2 shows a release behavior of BPS in Test 5 to determine the release of the preparations obtained in Examples 11 through 13 and Comparative Example 1, which test was carried out in 10 ml of a phosphate buffer solution (pH 7.4) at 37° C.

The resultes of release test are shown in FIG. 2. The results reveal that release of BPS from the preparation of the present invention was apparently controlled as compared to the Comparative Example and the release was delayed in correlation to the addition amount of benzalkonium chloride, which is a counter ion.

Test 5

Effect of the Addition Amount of Benzalkonium Chloride in Rat In Vivo:

The gel preparations obtained in Example 17 and Comparative Example 4 were subcutaneously given to Wistar strain male rats (age of 8 weeks) at the back, respectively. The concentration of the active substance in plasma was determined with passage of time.

Figure 3:
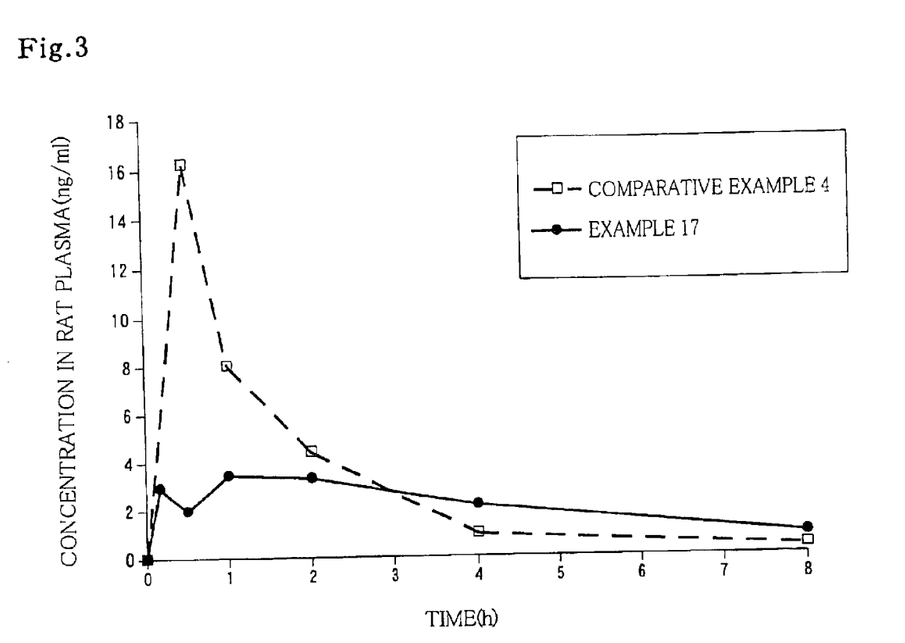
FIG. 3 shows the concentration of medicaments in plasma plotted with passage of time in Test 6, when the preparations obtained in Example 17 and Comparative Example 4 were subcutaneously given to Wistar strain male rats (age of 8 weeks) at the back.

The results of plasma concentration with passage of time are shown in FIG. 3. In the preparation of the present invention (added with benzalkonium chloride), the change in plasma concentration of the active substance showed a sustained release as compared to the comparative example. It is considered also from the foregoing results in vitro (Test 5) that the sustained release pattern can be controlled by changing the amount of benzalkonium chloride added.

EXAMPLE 18

Liquid Preparation:

In 99.638 parts of water, 0.002 part of BPS and 0.36 part of benzalkonium chloride were dissolved to give a liquid preparation.

COMPARATIVE EXAMPLE 5

Liquid Preparation:

A liquid preparation for comparison was prepared in a manner similar to Example 18 except that no benzalkonium chloride was added.

EXAMPLE 19

Emulsion Preparation:

After 0.002 part of BPS and 0.36 part of benzalkonium chloride were dissolved in 94.638 parts of water, 5 parts of soybean oil was added to the solution. An emulsion preparation was prepared using a microfluidizer (12,000 psi, 10 minutes at room temperature).

EXAMPLES 20 THROUGH 24

Emulsion Preparation:

Emulsion preparations having the amounts of BPS, benzalkonium chloride, other additives (surfactant, oil, etc.) and water shown in Table 5 were prepared in a manner similar to Example 19.

TABLE 5

| | Example | | | | |
|---|---|---|---|---|---|
| | 20 | 21 | 22 | 23 | 24 |
| BPS | 0.002 | 0.002 | 0.002 | 0.002 | 0.002 |
| Benzalkonium chloride | 0.36 | 0.36 | 0.36 | 0.36 | 0.36 |
| Pluronic F68 | 1.8 | — | — | 1.8 | — |
| Tween 80 | — | 1.8 | — | — | 1.8 |
| Soybean oil | 10 | 10 | — | — | — |
| Sesame oil | — | — | 5 | 10 | 10 |
| Concentrated glycerin | 2.21 | 2.21 | — | 2.21 | 2.21 |
| Water to make | 100 | 100 | 100 | 100 | 100 |

EXAMPLE 25

After 0.002 part of BPS and 0.36 part of benzalkonium chloride were dissolved in 2 parts of ethanol, soybean oil was added to the solution to make the volume 100 parts. Thus, an oily preparation was prepared.

EXAMPLES 26 THROUGH 30

Oily Preparation:

After BPS and benzalkonium chloride were dissolved in alcohols (ethanol, benzyl alcohol, benzyl benzoate), oil (soybean oil, sesame oil) was added to the solution, all in the amount indicated in Table 6, to make the volume 100 parts. Thus, oily preparations were prepared.

TABLE 6

| | Example | | | | |
|---|---|---|---|---|---|
| | 26 | 27 | 28 | 29 | 30 |
| BPS | 0.002 | 0.002 | 0.002 | 0.002 | 0.002 |
| Benzalkonium chloride | 0.36 | 0.36 | 0.36 | 0.36 | 0.36 |
| Ethanol | — | — | 2 | — | — |
| Benzyl alcohol | 2 | 5 | — | 2 | 5 |
| Benzyl benzoate | 20 | — | — | 20 | — |
| Soybean oil to make | 100 | 100 | — | — | — |
| Sesame oil to make | — | — | 100 | 100 | 100 |

EXAMPLES 31 THROUGH 34

Gel Preparation:

After 0.002 part of BPS and 0.36 part of benzalkonium chloride were dissolved in water, a gel base (CMC-Na, sodium hyaluronate, atherocollagen, gelatin) was added to the solution. The mixture was completely swollen to give gel preparations (Table 7).

TABLE 7

| | Example | | | |
|---|---|---|---|---|
| | 31 | 32 | 33 | 34 |
| BPS | 0.002 | 0.002 | 0.002 | 0.002 |
| Benzalkonium chloride | 0.36 | 0.36 | 0.36 | 0.36 |
| CMC-Na | 3 | — | — | — |
| Na hyaluronate | — | 2.5 | — | — |
| Atherocollagen | — | — | 2 | — |
| Gelatin | — | — | — | 10 |
| Water | 96.638 | 97.138 | 97.638 | 89.638 |

EXAMPLES 35 THROUGH 38

Cream Preparation:

After 0.002 part of BPS and 0.36 part of benzalkonium chloride were dissolved in water, a gel base (HPC-M, CMC-Na, sodium hyaluronate, atherocollagen) was added to the solution. The mixture was stirred to give cream preparations (Table 8).

TABLE 8

| | Example | | | |
|---|---|---|---|---|
| | 35 | 36 | 37 | 38 |
| BPS | 0.002 | 0.002 | 0.002 | 0.002 |
| Benzalkonium chloride | 0.36 | 0.36 | 0.36 | 0.36 |
| HPC-M | 5 | — | — | — |
| CMC-Na | — | 3 | — | — |
| Na hyaluronate | — | — | 2.5 | — |
| Atherocollagen | — | — | — | 2 |
| Water | 74.638 | 76.638 | 77.138 | 77.638 |
| Soybean oil | 20 | 20 | 20 | 20 |

Test 6
In Vivo Effect in Rat:

Each of the liquid preparations obtained in Example 18 and Comparative Example 5, the emulsion preparations of Examples 19 to 21, the oily preparations obtained in Examples 25 to 28 and the gel preparations or cream preparations obtained in Examples 31 to 38 was given to Wistar strain male rats (age of 8 weeks) at the back to determine the concentration of the medicament in plasma with passage of time.

The results reveal that the sustained release effect was obtained with the respective preparations, by adding counter ions. To the contrary, no sustained release effect was noted with some of the Comparative Examples.

EXAMPLE 39
Oily Preparation:

After 0.024 part of BPS was dissolved in 2 parts of benzyl alcohol, 20 parts of benzyl benzoate as a solubilizing agent was further added to the solution. Thereafter 0.36 part of benzalkonium chloride was added to the solution to dissolve therein. Sesame oil was added to the solution to make the volume 100 parts and give an oily preparation.

EXAMPLE 40
Gel Preparation with Low Viscosity:

In 92.192 parts of water were dissolved 0.048 part of BPS, 5.04 parts of D-sorbitol, 40.2 parts of dextran and 0.72 part of benzalkonium chloride to give a low viscosity gel preparation.

EXAMPLE 41
Emulsion Preparation:

In 83.076 parts of water were dissolved 0.024 part of BPS, 2 parts of Tween 80, 4.54 parts of D-sorbitol and 0.36 part of benzalkonium chloride. After 10 parts of sesame oil was added to the solution, the mixture was emulsified with an emulsifier (DeBee 2000, 23,000 psi, 2 pass) to give an emulsion preparation.

Industrial Applicability

The present invention is useful as providing the sustained-release pharmaceutical composition which exhibits excellent sustained release effect of the ionic prostanoic acid derivative, irrespective of water solubility of the ionic prostanoic acid derivative. The sustained release according to the present invention is effected by means of a technique quite different from conventional techniques including those adopted to retard the release of ionic prostanoic acid derivative, to insolubilize a prostanoic acid derivative itself and to retard dissolution of such a prostanoic acid derivative through microencapsulation. The present invention is also useful in that the sustained release can be achieved by the invention to a fully satisfactory extent that was not obtained by known techniques.

The pharmaceutical composition of the present invention can attain excellent sustained release effect not only in the form of injection but also in all other pharmaceutical preparations including implants, transmucosal and oral preparations.

What is claimed is:
1. A sustained-release pharmaceutical composition consisting essentially of an ionic prostaglandin $I_2$ derivative of the following general formula (I):

and an ionic compound having an opposite charge to that of the ionic prostaglandin $I_2$ derivative, which increases the oil/water partition coefficient of the ionic prostaglandin $I_2$ derivative, wherein
$R^1$ represents $COOR^2$ (wherein $R^2$ represents:
1) hydrogen or a pharmacologically acceptable cation,
2) —Z—$Ar_1$, wherein Z is a valence bond or a straight or branched alkylene shown by $C_tH_{2t}$, wherein t is an integer of 1 to 6, and $Ar^1$ is 2-pyridyl, 3-pyridyl or 4-pyridyl;
3) —$C_tH_{2t}COOR^3$, wherein $C_tH_{2t}$ has the same significance as defined above, and $R^3$ is hydrogen or a pharmacologically acceptable cation;

or,
4) —$C_tH_{2t}N(R^4)_2$, wherein $C_tH_{2t}$ has the same significance as defined above, and $R^4$ is hydrogen, a straight alkyl having 1 to 12 carbon atoms or a branched alkyl having 3 to 14 carbon atoms);
A represents:
1) —$(CH_2)_m$—, wherein m is an integer of 1 to 3;
2) —CH=CH—$CH_2$—;
3) —$CH_2$—CH=CH—;
4) —$CH_2$—O—$CH_2$—;
5) —CH=CH—;
6) —O—$CH_2$—; or,
7) —C≡C—;
Y represents hydrogen, an alkyl having 1 to 4 carbon atoms, chlorine, bromine, fluorine, formyl, methoxy or nitro;
B represents —X—$C(R^5)(R^6)OR^7$ (wherein $R^5$ represents hydrogen or an alkyl having 1 to 4 carbon atoms; $R^7$ represents hydrogen, an acyl having 1 to 14 carbon atoms, an aroyl having 6 to 15 carbon atoms, tetrahydropyranyl, tetrahydrofuranyl, 1-ethoxyethyl or t-butyl; X represents:
1) —$CH_2$—$CH_2$—;
2) —CH=CH—; or
3) —C≡C—;
$R^6$ represents:
1) a straight alkyl having 1 to 12 carbon atoms or a branched alkyl having 3 to 14 carbon atoms;
2) —Z—$Ar^2$ wherein Z has the same significance as defined above and $Ar^2$ is phenyl, α-naphthyl, β-naphthyl or a phenyl substituted with at least one of chlorine, bromine, fluorine, iodine, trifluoromethyl, an alkyl having 1 to 4 carbon atoms, nitro, cyano, methoxy, phenyl or phenoxy;
3) —$C_tH_{2t}OR^8$, wherein $C_tH_{2t}$ has the same significance as defined above, and $R^8$ is a straight alkyl having 1 to 6 carbon atoms, a branched alkyl having 3 to 6 carbon atoms, phenyl, a phenyl substituted with at least one of chlorine, bromine, fluorine, iodine, trifluoromethyl, an alkyl having 1 to 4 carbon atoms, nitro, cyano, methoxy, phenyl or phenoxy, cyclopentyl, cyclohexyl, or a cyclopentyl or cyclohexyl substituted with 1 to 4 straight alkyl group(s) having 1 to 4 carbon atoms;
4) —Z—$R^9$, wherein Z has the same significance as defined above, and $R^9$ is hydrogen, a cycloalkyl having 3 to 12 carbon atoms or a substituted cycloalkyl having 3 to 12 carbon atom which is substituted with 1 to 3 alkyl groups having 1 to 5 carbon atoms;
5) —$C_tH_{2t}$—CH=$C(R^{10})R^{11}$, wherein $C_tH_{2t}$ has the same significance as defined above, and $R^{10}$ and $R^{11}$ represent hydrogen, methyl, ethyl, propyl or butyl; or
6) —$C_uH_{2u}$—C≡C—$R^{12}$, wherein u is an integer of 1 to 7, $C_uH_{2u}$ is a straight or branched alkylene and $R^{12}$ is a straight alkyl having 1 to 6 carbon atoms);

E represents hydrogen or OR$^{13}$, wherein R$^{13}$ is hydrogen, an acyl having 1 to 12 carbon atoms, an aroyl having 7 to 18 carbon atoms, a straight alkyl having 1 to 12 carbon atoms or a branched alkyl having 3 to 14 carbon atoms; or a salt thereof, wherein the ionic compound is a compound containing a group selected from an ammonium, pyridinium, phosphonium and sulfonium group in the molecule thereof, or a salt thereof, or alternatively, a compound containing a carboxyl, sulfate, sulfonate or phosphate group in the molecule thereof, or a salt thereof, with optionally at least one additional component selected from the group consisting of vegetable oil, fatty acid triglycerides, fatty acid esters, polysiloxanes, hyaluronic acid or a salt thereof, hydroxypropylcellulose and atherocollagen.

2. A sustained-release pharmaceutical composition according to claim 1, wherein the ionic compound contains at least one member selected from the group consisting of an alkyldimethylbenzylammonium salt, an alkyltrimethylammonium salt, an alkylpyridinium salt, an alkylamine salt and an alkylphosphonium salt.

3. A sustained-release pharmaceutical composition according to claim 2, wherein the ionic compound is benzalkonium chloride.

4. A sustained-release pharmaceutical composition according to claim 1, wherein the prostaglandin I$_2$ derivative is (±)-(1R*-2R*, 3aS*, 8bS*)-2,3,3a,8b-tetrahydro-2-hydroxy-1-[(E)-(3D*)-3-hydroxy-4-methyl-1-octen-6-ynyl]-1H-cyclopenta[b]benzofuran-5-butanoic acid, or a salt thereof.

5. A sustained-release pharmaceutical composition according to claim 1, wherein the composition is formulated with at least one additional component selected from the group consisting of vegetable oil, fatty acid triglycerides, fatty acid esters, polysiloxanes, hyaluronic acid or a salt thereof, hydroxypropylcellulose and atherocollagen.

6. A sustained-release pharmaceutical composition according to claim 5, wherein the composition is formulated with at least one additional component selected from the group consisting of soybean oil, sesame oil, hyaluronic acid or a salt thereof, hydroxypropylcellulose and atherocollagen.

7. A sustained-release pharmaceutical composition for an ionic prostanoic acid derivative consisting essentially of an prostanoic acid derivative and an ionic compound having an opposite charge to that of the ionic prostanoic acid derivative and increasing hydrophobicity of the prostanoic acid derivative, wherein said ionic compound contains a carboxyl, sulfate, sulfonate or phosphate group in the molecule thereof, or a salt thereof, and wherein said prostanoic acid derivative is of the formula:

wherein
R$^1$ represents COOR$^2$ (wherein R$^2$ represents:
1) hydrogen or a pharmacologically acceptable cation,
2) —Z—Ar$_1$, wherein Z is a valence bond or a straight or branched alkylene shown by C$_t$H$_{2t}$ wherein t is an integer of 1 to 6, and Ar$^1$ is 2-pyridyl, 3-pyridyl or 4-pyridyl;

3) —C$_t$H$_{2t}$COOR$^3$, wherein C$_t$H$_{2t}$ has the same significance as defined above, and R$^3$ is hydrogen or a pharmacologically acceptable cation;
or,
4) —C$_t$H$_{2t}$ N(R$^4$)$_2$, wherein C$_t$H$_{2t}$ has the same significance as defined above, and R$^4$ is hydrogen, a straight alkyl having 1 to 12 carbon atoms or a branched alkyl having 3 to 14 carbon atoms);

A represents:
1) —(CH$_2$)$_m$—, wherein m is an integer of 1 to 3;
2) —CH=CH—CH$_2$;
3) —CH$_2$—CH=CH—;
4) —CH$_2$—O—CH$_2$—;
5) —CH=CH—;
6) —O—CH$_2$—; or,
7) C≡C—;

Y represents hydrogen, an alkyl having 1 to 4 carbon atoms, chlorine, bromine, fluorine, formyl, methoxy or nitro;

B represents —X—C(R$^5$)(R$^6$)OR$^7$ (wherein R$^5$ represents hydrogen or an alkyl having 1 to 4 carbon atoms; R$^7$ represents hydrogen, an acyl having 1 to 14 carbon atoms, an aroyl having 6 to 15 carbon atoms, tetrahydropyranyl, tetrahydrofuranyl, 1-ethoxyethyl or t-butyl; X represents:
1) —CH$_2$—CH$_2$—;
2) —CH=CH—; or
3) —C≡C—;

R$^6$ represents:
1) a straight alkyl having 1 to 12 carbon atoms or a branched alkyl having 3 to 14 carbon atoms;
2) —Z—Ar$^2$ wherein Z has the same significance as defined above and Ar$^2$ is phenyl, α-naphthyl, β-naphthyl or a phenyl substituted with at least one of chlorine, bromine, fluorine, iodine, trifluoromethyl, an alkyl having 1 to 4 carbon atoms, nitro, cyano, methoxy, phenyl or phenoxy;
3) —C$_t$H$_{2t}$OR$^8$, wherein C$_t$H$_{2t}$ has the same significance as defined above, and R$^8$ is a straight alkyl having 1 to 6 carbon atoms, a branched alkyl having 3 to 6 carbon atoms, phenyl, a phenyl substituted with at least one of chlorine, bromine, fluorine, iodine, trifluoromethyl, an alkyl having 1 to 4 carbon atoms, nitro, cyano, methoxy, phenyl or phenoxy, cyclopentyl, cyclohexyl, or a cyclopentyl or cyclohexyl substituted with 1 to 4 straight alkyl group(s) having 1 to 4 carbon atoms;
4) —Z—R$^9$, wherein Z has the same significance as defined above, and R$^9$ is hydrogen, a cycloalkyl having 3 to 12 carbon atoms or a substituted cycloalkyl having 3 to 12 carbon atom which is substituted with 1 to 3 alkyl groups having 1 to 5 carbon atoms;
5) —C$_t$H$_{2t}$CH=C(R$^{10}$)R$^{11}$, wherein C$_t$H$_{2t}$ has the same significance as defined above, and R$^{10}$ and R$^{11}$ represent hydrogen, methyl, ethyl, propyl or butyl; or
6) —C$_u$H$_{2u}$—C≡C—R$^{12}$, wherein u is an integer of 1 to 7, C$_u$H$_{2u}$ is a straight or branched alkylene and R$^{12}$ is a straight alkyl having 1 to 6 carbon atoms);

E represents hydrogen or OR$^{13}$, wherein R$^{13}$ is hydrogen, an acyl having 1 to 12 carbon atoms, an aroyl having 7 to 18 carbon atoms, a straight alkyl having 1 to 12 carbon atoms or a branched alkyl having 3 to 14 carbon atoms; or a salt thereof and optionally the composition is formulated with at least one additional component selected from the group consisting of vegetable oil, fatty acid triglycerides, fatty acid esters, polysiloxanes, hyaluronic acid or a salt thereof, hydroxypropylcellulose and atherocollagen.

8. A sustained-release pharmaceutical composition according to claim 7, wherein the ionic compound is sodium laurylsulfate and/or sodium oleate.

9. A sustained-release pharmaceutical composition according to claim 7, wherein the composition is formulated with at least one additional component selected from the group consisting of vegetable oil, fatty acid triglycerides, fatty acid esters, polysiloxanes, hyaluronic acid or a salt thereof, hydroxypropylcellulose and atherocollagen.

10. A sustained-release pharmaceutical composition according to claim 9, wherein the composition is formulated with at least one additional component selected from the group consisting of soybean oil, sesame oil, hyaluronic acid or a salt thereof, hydroxypropylcellulose and atherocollagen.

* * * * *